US009744382B2

(12) United States Patent
Sauermann et al.

(10) Patent No.: US 9,744,382 B2
(45) Date of Patent: Aug. 29, 2017

(54) COSMETIC AND DERMATOLOGICAL PREPARATIONS CONTAINING CARNITINE FOR TREATING AND ACTIVELY PREVENTING DRY SKIN AND OTHER NEGATIVE ALTERATIONS IN THE PHYSIOLOGICAL HOMEOSTASIS OF HEALTHY SKIN

(75) Inventors: Gerhard Sauermann, Gross Neuendorf (DE); Volker Schreiner, Hamburg (DE); Thomas Döring, Dormagen (DE); Wilfried Siefken, Hamburg (DE); Cornelia Gatermann, Hamburg (DE); Stefanie Carstensen, Hamburg (DE); Helga Biergiesser, Reinbek (DE)

(73) Assignee: BEIERSDORF AG, Hamburg (DE)

( * ) Notice: Subject to any disclaimer, the term of this patent is extended or adjusted under 35 U.S.C. 154(b) by 2369 days.

(21) Appl. No.: 10/482,164

(22) PCT Filed: Jul. 4, 2002

(86) PCT No.: PCT/EP02/07423
§ 371 (c)(1),
(2), (4) Date: Aug. 13, 2004

(87) PCT Pub. No.: WO03/005980
PCT Pub. Date: Jan. 23, 2003

(65) Prior Publication Data
US 2004/0253282 A1    Dec. 16, 2004

(30) Foreign Application Priority Data
Jul. 7, 2001    (DE) .................................. 101 33 200

(51) Int. Cl.
| | | |
|---|---|---|
| *A61Q 19/00* | (2006.01) | |
| *A61K 8/06* | (2006.01) | |
| *A61K 8/34* | (2006.01) | |
| *A61K 8/42* | (2006.01) | |
| *A61K 8/44* | (2006.01) | |
| *A61K 8/49* | (2006.01) | |
| *A61K 31/205* | (2006.01) | |
| *A61Q 17/00* | (2006.01) | |
| *A61Q 19/08* | (2006.01) | |

(52) U.S. Cl.
CPC .............. *A61Q 19/005* (2013.01); *A61K 8/06* (2013.01); *A61K 8/345* (2013.01); *A61K 8/42* (2013.01); *A61K 8/44* (2013.01); *A61K 8/494* (2013.01); *A61K 31/205* (2013.01); *A61Q 17/00* (2013.01); *A61Q 19/00* (2013.01); *A61Q 19/007* (2013.01); *A61Q 19/08* (2013.01); *A61K 2800/75* (2013.01)

(58) Field of Classification Search
None
See application file for complete search history.

(56) References Cited

U.S. PATENT DOCUMENTS

| | | | |
|---|---|---|---|
| 3,949,087 A | 4/1976 | Bacq et al. | |
| 4,401,827 A * | 8/1983 | de Witt | 560/1 |
| 4,485,091 A * | 11/1984 | Fitton | 424/62 |
| 4,839,159 A | 6/1989 | Winter et al. | |
| 5,418,253 A * | 5/1995 | Cavazza et al. | 514/547 |
| 5,639,767 A | 6/1997 | Cavazza et al. | |
| 5,834,513 A | 11/1998 | Ptchelintsev et al. | |
| 5,922,331 A | 7/1999 | Mausner | |
| 5,939,082 A | 8/1999 | Oblong et al. | |
| 5,952,379 A * | 9/1999 | Fassi | 514/561 |
| 6,051,608 A * | 4/2000 | Santaniello et al. | 514/556 |
| 6,149,924 A | 11/2000 | Paul | |
| 6,245,378 B1 * | 6/2001 | Cavazza | 426/656 |
| 6,337,320 B1 | 1/2002 | Hersh et al. | |
| 6,432,424 B1 * | 8/2002 | Shapiro et al. | 424/401 |
| 2001/0031281 A1 * | 10/2001 | Kung et al. | 424/487 |
| 2002/0044913 A1 * | 4/2002 | Hamilton | 424/59 |
| 2003/0180277 A1 | 9/2003 | Hoppe et al. | |

FOREIGN PATENT DOCUMENTS

| | | |
|---|---|---|
| DE | 4401308 | 7/1995 |
| DE | 19618670 | 11/1997 |
| DE | 19806889 | 8/1999 |
| DE | 19806890 | 8/1999 |
| DE | 19806947 | 8/1999 |
| DE | 19806946 | 9/1999 |
| DE | 10036798 | 2/2002 |
| EP | 0628308 | 12/1994 |
| FR | 2797765 | * 3/2001 |
| JP | 8-127520 | 5/1996 |
| WO | 00/04870 | 2/2000 |
| WO | 01/82878 | 11/2001 |

OTHER PUBLICATIONS

English language abstract of DE 198 06 889 (provided by esp@cenet).
English language abstract of JP 8-127520 (provided by esp@cenet) and Database WPI abstract No. XP-002233382.
English language abstract of DE 196 18 670 (provided by esp@cenet).
English language abstract (provided by esp@cenet) of JP 11-302143 A, Nov. 2, 1999.
English language abstract Database WPI abstract No. XP-002233383 of JP 2001-220345 A, Aug. 14, 2001.
English language abstract of DE 198 06 947 (provided by esp@cenet).
English language abstract of DE 198 06 946 (provided by esp@cenet).
English language abstract of DE 198 06 890 (provided by esp@cenet).
English language abstract of DE 44 01 308 (provided by esp@cenet).
M.P. Elias, Structure and Function of the Stratum Corneum Permeability Barrier, Drug Dev. Res. 13, 1988, pp. 97-105.
U.S. Appl. No. 11/295,566, filed Dec. 7, 2005, and entitled "Active ingredient combinations of one or more isoflavonoids and carnitine and/or one or more acyl-carnitines".

* cited by examiner

*Primary Examiner* — Kyle Purdy
(74) *Attorney, Agent, or Firm* — Abel Law Group, LLP

(57) ABSTRACT

A cosmetic or dermatological composition which comprises carnitine, a precursor thereof, a metabolite thereof and/or a derivative thereof.

25 Claims, No Drawings

COSMETIC AND DERMATOLOGICAL PREPARATIONS CONTAINING CARNITINE FOR TREATING AND ACTIVELY PREVENTING DRY SKIN AND OTHER NEGATIVE ALTERATIONS IN THE PHYSIOLOGICAL HOMEOSTASIS OF HEALTHY SKIN

CROSS-REFERENCE TO RELATED APPLICATIONS

The present application is a U.S. National Stage of International Application No. PCT/EP02/07423, filed Jul. 4, 2002, which claims priority under 35 U.S.C. §119 of German Patent Application No. 101 33 200.9, filed Jul. 7, 2001.

BACKGROUND OF THE INVENTION

1. Field of the Invention

The present invention relates in particular to the use of carnitine and/or derivatives and precursors thereof and active ingredient combinations with one or more electrolytes and with glycerol and/or urea alone or in combination for the treatment and active prevention of dry skin and for strengthening the barrier function of the skin, and other negative changes in the physiological homeostasis of healthy skin.

2. Discussion of Background Information

The skin is the largest human organ. Amongst its many functions (for example for temperature regulation and as a sensory organ), the barrier function, the one which prevents the skin (and thus ultimately the entire organism) from drying out, is probably the most important. At the same time, the skin acts as a protective device against the penetration and absorption of external substances. This barrier function is effected by the epidermis which, as the outermost layer, forms the actual protective sheath against the environment. Being about one tenth of the total thickness, it is also the thinnest layer of the skin.

The epidermis is a stratified tissue in which the outer layer, the horny layer (*Stratum corneum*), is the part which is of significance for the barrier function. Being in contact with the environment, it is worn away and therefore finds itself in a continuous process of renewal, where, on the outside, fine flakes are continuously shed and, on the inside, keratinized cell and lipid material is subsequently produced.

The Elias skin model, which is currently recognized in the specialist field (P. M. Elias, *Structure and Function of the Stratum Corneum Permeability Barrier, Drug Dev. Res.* 13, 1988, 97-105), describes the horny layer as a two-component system, similar to a brick wall (bricks and mortar model). In this model, the horny cells (corneocytes) correspond to the bricks, and the lipid membrane, which is of complex composition, in the intercellular spaces corresponds to the mortar. This system essentially represents a physical barrier to hydrophilic substances, but, because of its narrow and multilayered structure, can equally, however, also be passed by lipophilic substances only with difficulty. The particular structure of the horny layer on the one hand protects the skin and on the other hand stabilizes its own flexibility by binding a defined amount of water.

Mechanical stresses, such as, for example, compressive forces, impact or shear forces, can also be intercepted to a surprising degree by the horny layer alone or in conjunction with the deeper layers of the skin. Relatively large compressive forces, torsional forces or shear forces are transmitted to deeper layers of the skin via the meshing of the epidermis with the corium.

The regulation of the water and moisture content is one of the most important functions of the epidermal lipid membrane. However, it not only has a barrier effect against external chemical and physical influences, but also contributes to the cohesion of the horny layer.

The lipids of the horny layer essentially consist of ceramides, free fatty acids, cholesterol and cholesterol sulphate and are distributed over the entire horny layer. The composition of these lipids is of decisive importance for the intact function of the epidermal barrier and thus for the water impermeability of the skin.

Even cleansing the skin using a simple waterbath—without the addition of surfactants—initially causes the horny layer of the skin to swell. The degree of this swelling depends, inter alia, on the bathing time and temperature. At the same time, water-soluble substances are washed off or out, such as e.g. water-soluble constituents of dirt, but also substances endogenous to the skin which are responsible for the water-binding capacity of the horny layer. In addition, as a result of surface-active substances which are endogenous to the skin, fats in the skin are also dissolved and washed out to a certain degree. After initial swelling, this causes a subsequent drying-out of the skin, which may be further considerably intensified by washing-active additives.

In healthy skin, these processes are generally of no consequence since the protective mechanisms of the skin are able to readily compensate for such slight disturbances to the upper layers of the skin. However, even in the case of nonpathological deviations from the norm, e.g. as a result of wear damage or irritations caused by the environment, photodamage, ageing skin etc., the protective mechanism on the surface of the skin is impaired.

In aged skin, for example, regenerative renewal takes place at a slower rate, where, in particular, the water-binding capacity of the horny layer decreases. The skin thus becomes inflexible, dry and chapped ("physiologically" dry skin). Barrier damage is the result. The skin becomes susceptible to negative environmental effects, such as the invasion of microorganisms, toxins and allergens. As a consequence, toxic or allergic skin reactions may even result.

In the case of pathologically dry and sensitive skin, barrier damage is present a priori. Epidermal intercellular lipids become defective or are formed in an inadequate amount or composition. The consequence is increased permeability of the horny layer and inadequate protection of the skin against loss of hygroscopic substances and water.

The barrier effect of the skin can be quantified via the determination of the transepidermal water loss (TEWL). This is the evaporation of water from inside the body without taking into account the loss of water during perspiration. Determination of the TEWL value has proven to be extraordinarily informative and can be used to diagnose chapped or cracked skin, for determining the compatibility of surfactants which have very different chemical structures, and more besides.

For the beauty and well-cared-for appearance of the skin, the proportion of water in the uppermost layer of the skin is of greatest significance. It can be favourably influenced within a limited scope by introducing moisture regulators.

Anionic surfactants, which are generally constituents of cleansing preparations, can lastingly increase the pH in the horny layer, which severely hinders regenerative processes which serve to restore and renew the barrier function of the skin. In this case, a new, frequently very unfavourable state of equilibrium is established in the horny layer between regeneration and the loss of essential substances as a result of regular extraction; this state has a decisive adverse effect on the outer appearance of the skin and the physiological mode of function of the horny layer.

For the purposes of the present invention, skin care is understood primarily as meaning that the natural function of the skin as a barrier against environmental influences (e.g. dirt, chemicals, microorganisms) and against the loss of substances endogenous to the body (e.g. water, lipids, electrolytes) is strengthened or restored.

Products for the care, treatment and cleansing of dry and stressed skin are known per se. However, their contribution to the regeneration of a physiologically intact, hydrated and smooth horny layer is limited with regard to extent and time.

The effect of ointments and creams on the barrier function and the hydration of the horny layer is based essentially on the coverage (occlusion) of the areas of skin treated. The ointment or cream represents, as it were, a (second) artificial barrier which is iritended to prevent loss of water by the skin. It is equally easy to remove this physical barrier, for example using cleansers, again, as a result of which the original, impaired state is again achieved. Moreover, the skin care effect can decrease upon regular treatment. After use of the product is stopped, the skin reverts very quickly to the state prior to the start of treatment. In the case of certain products, the condition of the skin is even temporarily worsened in some circumstances. A permanent product effect is therefore generally not achieved or is achieved only to a limited extent.

The effect of some pharmaceutical preparations on the barrier function of the skin consists even in selective damage to the barrier, which is intended to make it possible for active ingredients to be able to penetrate into or through the skin into the body. Here, a disturbed appearance of the skin as a side effect is accepted to some extent as a small price to pay.

The effect of caring cleansing products consists essentially in an efficient refatting with sebum lipid-like substances. The simultaneous reduction in the surfactant content of such preparations permits a further limitation of the damage to the horny layer barrier.

However, the prior art lacks preparations which have a positive effect on the barrier function and hydration of the horny layer and enhance or even restore the physicochemical properties of the horny layer and, in particular, of the lamellae comprising intercellular lipids.

In order to aid the skin in its natural regeneration and to strengthen its physiological function, intercellular lipid mixtures, such as ceramides or ceramide analogues, have recently increasingly been added to topical preparations which are to be used by the skin to rebuild the natural barrier. However, these lipids are mostly very expensive raw materials. In addition, their effect is in most cases very much lower than that hoped for.

The object of the present invention was therefore to overcome the disadvantages of the prior art. In particular, the aim was to provide skincare compositions which retain or restore the barrier properties of the skin, especially when the natural regeneration of the skin is inadequate. They should also be suitable for the treatment and prophylaxis of subsequent damage of the skin drying out, for example cracks or inflammatory or allergic processes, or also of neurodermatitis. The object of the present invention was also to provide stable skincare cosmetic and/or dermatological compositions which protect the skin against environmental influences such as sun and wind. In particular, the effect of the preparations should be physiological, rapid and long-lasting.

In addition, disturbances of the homeostasis of the skin, in particular healthy skin, should be treated and overcome or be prophylactically treated.

The objects posed are achieved according to the invention.

SUMMARY OF THE INVENTION

The present invention provides a cosmetic or dermatological composition which comprises from 0.001% to 30% by weight of carnitine, a precursor thereof, a metabolite thereof and/or a derivative thereof.

In one aspect, the carnitine, precursor, metabolite and/or derivative thereof may be present in a concentration of from 0.05% to 10% by weight, e.g., in a concentration of from 0.1% to 5.0% by weight.

In another aspect of the composition, the composition may comprise L-carnitine, and/or an acylcarnitine such as, e.g., acetyl-L-carnitine or propionyl-L-carnitine, and/or a carnitine ester such as, e.g., L-carnitine fumarate and L-carnitine galactarate. For example, it may comprise from 0.05% to 10% by weight of at least one of L-carnitine, acetyl-L-carnitine, propionyl-L-carnitine, L-carnitine fumarate and L-carnitine galactarate.

The present invention also provides a cosmetic or dermatological composition which comprises carnitine, a precursor thereof, a metabolite thereof and/or a derivative thereof, and further comprises at least one electrolyte.

In one aspect, the at least one electrolyte may comprise NaCl, NaBr, NaI, $Na_2B_4O_7$, $Na_2SiO_3$, $Na_2CO_3$, $NaHCO_3$, $Na_3PO_4$, $Na_2HPO_4$, $NaH_2PO_4$, KCl, KI, LiCl, $NH_4Cl$, $ZnCl_2$, $Al_2(SO_4)_3$, $MgSO_4$, sodium liponate, sodium citrate, ammonium lactate, sodium lactate, sodium bicarbonate, sodium propionate, or a combination of two or more thereof.

In another aspect, the at least one electrolyte may be present in a concentration of from 0.05% to 30% by weight, e.g., in a concentration of from 1% to 5% by weight.

In yet another aspect, the carnitine, precursor, metabolite and/or derivative thereof may be present in a concentration of from 0.1% to 5.0% by weight and the at least one electrolyte may be present in a concentration of from 1% to 5% by weight.

The present invention also provides a cosmetic or dermatological composition which comprises carnitine, a precursor thereof, a metabolite thereof and/or a derivative thereof, and further comprises at least one polyol and/or urea.

In one aspect, the composition may comprise glycerol. In another aspect, it may comprise both a polyol and urea.

In another aspect of the composition, the polyol may comprise at least one of glycerol, a butylene glycol, a propylene glycol, ethylene glycol, a pentanediol, a hexanediol, diethylene glycol, triethylene glycol, dipropylene glycol, tripropylene glycol, dibutylene glycol, and tributylene glycol.

In yet another aspect, the at least one polyol may be present in a concentration of from 0.05% to 30% by weight, e.g., in a concentration of from 0.1% to 20% by weight.

In a still further aspect of the composition, the urea may be present in a concentration of from 0.05% to 30% by weight, e.g., in a concentration of from 0.1% to 20% by weight.

In another aspect, the at least one polyol and the urea may be present in a total concentration of from 0.05% to 30% by weight, e.g., in a total concentration of from 0.1% to 20% by weight.

In yet another aspect, the weight ratio polyol:urea may be from 1:2 to 2:1.

In a still further aspect, the carnitine, precursor, metabolite and/or derivative thereof may be present in a concentration of from 0.1% to 5.0% by weight.

In another aspect of the composition, the carnitine, precursor, metabolite and/or derivative thereof may be present in a concentration of from 0.001% to 30% by weight and may comprise at least one of L-carnitine, acetyl-L-carnitine, propionyl-L-carnitine, L-carnitine fumarate and L-carnitine galactarate.

In yet another aspect, the composition may further comprise at least one electrolyte, for example, at least one of NaCl, NaBr, NaI, $Na_2B_4O_7$, $Na_2SiO_3$, $Na_2CO_3$, $NaHCO_3$, $Na_3PO_4$, $Na_2HPO_4$, $NaH_2PO_4$, KCl, KI, LiCl, $NH_4Cl$, $ZnCl_2$, $Al_2(SO_4)_3$, $MgSO_4$, sodium liponate, sodium citrate, ammonium lactate, sodium lactate, sodium bicarbonate and sodium propionate. Further, the at least one electrolyte may be present in a concentration of from 0.05% to 30% by weight.

In a still further aspect of this composition, the carnitine, precursor, metabolite and/or derivative thereof may be present in a concentration of from 0.1% to 5.0% by weight and the at least one electrolyte may be present in a concentration of from 1% to 5% by weight.

In yet another aspect, the composition may comprise NaCl and glycerol.

The present invention also provides a cosmetic or dermatological composition which comprises carnitine, a precursor thereof, a metabolite thereof and/or a derivative thereof, and further comprises at least one osmolyte.

In one aspect, the osmolyte may comprise a sugar alcohol, a methylamine compound, an amino acid and/or precursors thereof.

In another aspect, the carnitine, precursor, metabolite and/or derivative thereof may be present in a concentration of from 0.001% to 30% by weight and the osmolyte may comprise myoinositol, mannitol, sorbitol, taurine, choline, betaine, phosphorylcholine, a glycerophosphorylcholine, glutamine, glycine, α-alanine, glutamate, aspartate, proline, or a combination of two or more thereof.

In yet another aspect, the carnitine, precursor, metabolite and/or derivative thereof may be present in a concentration of from 0.05% to 10% by weight and may comprise at least one of L-carnitine, acetyl-L-carnitine, propionyl-L-carnitine, L-carnitine fumarate and L-carnitine galactarate.

In a still further aspect, the composition may further comprises at least one polyol and/or urea. For example, the composition may comprise glycerol.

In yet another aspect, the composition may further comprise at least one electrolyte. The at least one electrolyte may comprise, for example, NaCl, NaBr, NaI, $Na_2B_4O_7$, $Na_2SiO_3$, $Na_2CO_3$, $NaHCO_3$, $Na_3PO_4$, $Na_2HPO_4$, $NaH_2PO_4$, KCl, KI, LiCl, $NH_4Cl$, $ZnCl_2$, $Al_2(SO_4)_3$, $MgSO_4$, sodium liponate, sodium citrate, ammonium lactate, sodium lactate, sodium bicarbonate, sodium propionate, or a combination of two or more thereof. For example, the composition may comprise NaCl in a concentration of from 1% to 5% by weight.

In a still further aspect, the composition may further comprise at least one polyol and/or urea. For example, the composition may comprise glycerol.

The present invention also provides a method for the cosmetic or dermatological treatment of skin, wherein the method comprises applying onto at least parts of the skin any of the compositions discussed above, including the various aspects thereof.

In one aspect of the method, the cosmetic or dermatological treatment may comprise the treatment and/or active prevention of dry skin, and/or a strengthening of the barrier function of the skin, and/or the treatment, care and/or prophylaxis of sensitive skin, and/or the treatment or prophylaxis of symptoms of a negative change in the physiological homeostasis of healthy skin.

In another aspect, the cosmetic or dermatological treatment may comprise the treatment and/or prophylaxis of deficient, sensitive or hypoactive skin conditions, and/or of deficient, sensitive or hypoactive conditions of skin appendages and/or of inflamed skin conditions.

In yet another aspect, the cosmetic or dermatological treatment may comprise the treatment and/or prophylaxis of atopic eczema and/or polymorphous photodermatosis and/or psoriasis and/or vitiligo and/or of sensitive, itching or irritated skin.

In a still further aspect, the cosmetic or dermatological treatment may comprise the treatment and/or prophylaxis of a change in normal lipid peroxidation and/or a change in the ceramide, lipid and energy metabolism of healthy skin and/or a change in the physiological transepidermal water loss and/or a reduction in skin hydration and/or a decrease in the moisture content of the skin and/or a change in the natural moisturizing factor content and/or a reduction in the cell-cell communication.

In another aspect of the method, the cosmetic or dermatological treatment may comprise the treatment and/or prophylaxis of deficiency symptoms of intracellular DNA synthesis and/or of DNA damage and reduction in endogenous DNA repair mechanisms and/or of deviations from normal post-translational modifications of connective tissue constituents.

In yet another aspect, the cosmetic or dermatological treatment may comprise the treatment and/or prophylaxis of changes in the normal hyaluronic acid and giucosaminoglycan content of the healthy skin and/or of dandruff formation by hair and/or of a flaking of the scalp and of skin ageing.

In a still further aspect, the cosmetic or dermatological treatment may comprise an activation of metalloproteinases and/or other proteases, and/or an inhibition of corresponding endogenous DNA repair mechanisms.

As stated, the objects of the present invention included to overcome the above-mentioned disadvantages of the prior art.

These objects are achieved, in a manner which is surprising and could not have been foreseen by the person skilled in the art, through the use of preparations to be applied topically having a content of
 a) one or more compounds from the group formed by carnitine and precursors and derivatives and metabolic metabolites thereof,
 b) optionally one or more compounds from the group of electrolytes,
 c) optionally one or more compounds from the group formed by polyols and urea, and optionally
 d) one or more compounds from the group of osmolytes,
 for the treatment and active prevention of dry skin, and for strengthening the barrier function of the skin, and for the treatment, care and prophylaxis of sensitive skin and/or for the treatment and prophylaxis of the symptoms of a negative change in the physiological homeostasis of healthy skin, in particular of deficient, sensitive or hypoactive skin conditions or deficient, sensitive or hypoactive conditions of skin appendages,
 inflamed skin conditions, and of atopic eczema, polymorphous photodermatosis, psoriasis, vitiligo,
 sensitive, itching or irritated skin,
 changes in normal lipid peroxidation,
 a change in the ceramide, lipid and energy metabolism of healthy skin, a change in the physiological transepidermal water loss,
a reduction in skin hydration and decrease in the moisture content of the skin,
change in the natural moisturizing factor content,
reduction in cell-cell communication,
deficiency symptoms of intracellular DNA synthesis,
DNA damage and reduction in endogenous DNA repair mechanisms,
activation of metalloproteinases and/or other proteases or inhibition of the corresponding endogenous DNA repair mechanisms,
deviations from the normal post-translational modifications of connective tissue constituents,
changes in the normal hyaluronic acid and glucosaminoglycan content of healthy skin and dandruff formation by the hair.

Preference is given to cosmetic and dermatological topical preparations, in particular cosmetic topical preparations.

The structure of human hair is essentially the same as that of the horny layer of human skin. Between the dead corneocytes there are lipids, such as, for example, ceramides, which counteract the drying out and structural weakening of the hair. Thus, the active ingredients according to the invention and combinations thereof can also improve the structure of the hair. Moreover, the active ingredients according to the invention and combinations thereof are also suitable for the treatment of a flaky scalp.

Skin ageing, particularly if promoted by chronic solar irradiation, represents, for example, a particularly dramatic form of the disturbance of skin homeostasis. Surprisingly, the active ingredients according to the invention and combinations thereof improve very particularly homeostatic deviations of ageing skin. They are therefore, like the preparations which comprise them, very readily suitable for the treatment and prophylactic treatment of skin ageing.

The invention also provides for the use of the active ingredients according to the invention.

Preferably, the preparations according to the invention comprise one or more of the compounds of group a) and one or more compounds of the group b) or of group c).

Particular preference is given to preparations with a content of in each case one or more compounds of groups a) and b) and c).

Osmolytes are understood here as meaning osmotically active, uncharged molecules which can be taken up, actively or else passively, by epidermal keratinocytes.

The compounds according to the invention can optionally be used as acids or in the form of their salts, e.g. water-soluble salts, e.g. sodium or potassium salts.

Precursors are, for example, compounds which are converted into the active ingredients by metabolic steps.

Preference is given to L-carnitine and derivatives, precursors and metabolites thereof.

Preferred derivatives are acylcarnitine (O-acyl) and carnitine esters, e.g. with carboxylic acids.

Suitable acyl groups are e.g. alkylcarbonyl groups with 2-12, in particular 2-6, carbon atoms. Particular preference is given to acetyl-L-carnitine and propionyl-L-carnitine.

Suitable carboxylic acids are e.g. fumaric acid or galactaric acid. Particular preference is given to L-carnitine fumarate and L-carnitine galactarate.

The carbonyl group of the carnitines can also be esterified with alkanols having e.g. 1-10, preferably 1-5, in particular 1-3, carbon atoms.

The active ingredients of group a) are advantageously present in cosmetic or dermatological preparations, for example, in amounts of from 0.001% by weight to 30% by weight, preferably in amounts of from 0.05% by weight to 10% by weight, particularly preferably in amounts of 0.1-5.0% by weight, based on the total weight of the preparations.

Suitable electrolytes are compounds which are capable of dissociating into ions, in particular upon dissolution in water. They may, for example, be in the form of inorganic or organic salts.

Preference is given to the use of inorganic salts (in particular NaCl, NaBr, NaI, $Na_2B_4O_7$, $Na_2SiO_3$, $Na_2CO_3$, $NaHCO_3$, $Na_3PO_4$, $Na_2HPO_4$, $NaH_2PO_4$, KCl, KI, LiCl, $NH_4Cl$, $ZnCl_2$, $Al_2SO_4$ and $MgSO_4$), and of salts of organic acids, in particular of acids which occur naturally in the skin, e.g. of energy metabolism, such as sodium lipoate, sodium citrate, ammonium lactate, sodium lactate, sodium bicarbonate or weak carboxylic acids, e.g. sodium propionate. Surprisingly, the activity system mentioned stimulates the skin's own metabolism of lipids and proteins which have to be constantly regenerated to maintain the epidermal barrier to water. According to the invention, dry skin in particular is treated and/or cared for by the barrier-strengthening effect of these preparations, while normal skin is actively prevented from drying out.

Cosmetic or dermatological preparations according to the invention preferably comprise 0.05-30% by weight, particularly preferably 1-5% by weight, of one or more electrolytes, preferably sodium chloride, based on the total composition of the preparations.

Suitable osmolytes are, for example, the polyols, methylamine compounds and amino acids, and in each case precursors thereof.

The osmolytes used are, according to the invention, in particular substances from the group of sugar alcohols (myoinositol, mannitol, sand/or one or more of the osmolytically active substances specified belowcholine, betaine, phosphorylcholine, glycerophosphorylcholines, glutamine, glycineaegeaepe and taurine. Precursors of these substances are, for example, glglucose polymers, phosphatidylcholine, phosphatidylinositol, inorganic phosphates, proteins, peptides and polyamine acids. Precursors are, for example, compounds which are converted into osmolytes by metabolic steps. β-Alanin
L-Carnitin Said osmolytes and/or precursors thereof are, according to the invention, advantageously present in cosmetic or dermatological preparations preferably in amounts of from 0.001% by weight to 30% by weight, preferably 0.05% by weight to 10% by weight, particularly preferably 0.1-5.0% by weight, based on the total weight of the preparations.

Preference is given to preparations which comprise polyol, in particular glycerol, and urea at the same time.

Suitable polyols are, for example, straight-chain, branched or cyclic alkanols having, for example, 2-6 OH groups, preferably 2 or 3 OH groups and e.g. 2-12 or 2-6, in particular 2 or 3 or 4, carbon atoms.

Of high suitability are, for example, glycols, including those with non-vicinal OH groups and also polyalkylene glycols, e.g. with 2-6, in particular 2, 3 or 4 carbon atoms per glycol unit, which may be etherified in the same way or in a mixed fashion. The number of alkylglycol units in the polyalkylene glycol may, for example, be up to 20, preferably up to 10, but in particular 2, 3, 4 or 5.

Glycerol, butylene glycols, propylene glycols, ethylene glycol, pentanediols, hexanediols, in particular in each case the vicinal hydroxy compounds, diethylene glycol, triethylene glycol, dipropylene glycol, tripropylene glycol, dibutylene glycol and tributylene glycol are particularly suitable.

According to the invention, polyols are advantageously present in cosmetic or dermatological preparations e.g. in amounts of from 0.05% by weight to 30% by weight, preferably 0.1% by weight to 20% by weight, particularly preferably 1-15% by weight, based on the total weight of the preparations.

According to the invention, urea is advantageously present in cosmetic or dermatological preparations e.g. in amounts of from 0.05% by weight to 30% by weight, preferably 0.1% by weight to 20% by weight, particularly preferably 1-15% by weight, based on the total weight of the preparations.

For the combination of polyol and urea, according to the invention these substances are advantageously present in cosmetic or dermatological preparations e.g. in amounts of from 0.05% by weight to 30% by weight, preferably 0.1% by weight to 20% by weight, particularly preferably 1-15% by weight, based on the total weight of the preparations.

The ratio of the weight of the active ingredients of group b) (electrolytes) to the weight of the active ingredients of group c) can vary. For example, the b)/c) weight ratio can be from 10:1 to 1:10, preferably 2:1 to 1:2, but in particular 1:1.

For the combination of polyol and urea, the ratio of the weight of the polyol to the weight of the urea can vary. For example, the polyol/urea weight ratio may be from 1:10 to 10:1, preferably 2:1 to 1:2, but in particular 1:1.

Surprisingly, the activity system mentioned stimulates the skin's own metabolism of lipids and proteins which have to be constantly regenerated to maintain the epidermal barrier to water. According to the invention, the dry skin is treated and/or cared for by the barrier-strengthening effect of these preparations, while normal skin is actively prevented from drying out.

In every respect the preparations according to the invention are extremely satifactory preparations. It had been unforeseen for the person skilled in the art that the preparations according to the invention better retain or restore the barrier properties of the skin,
strengthen the ceramide biosynthesis of the skin,
better counteract drying-out of the skin,
better counteract skin ageing and
better protect the skin against environmental influences than the preparations of the prior art.

The cosmetic or dermatological preparations according to the invention can have the customary composition and be used for the treatment, care and cleansing of the skin and/or hair and as a make-up product in decorative cosmetics. Accordingly, depending on their formulation, they may be used, for example, as skin protection cream, cleansing milk, sunscreen lotion, nutrient cream, day or night cream etc. It is optionally possible and advantageous to use the preparations according to the invention as a basis for pharmaceutical formulations. The preparations according to the invention comprise, for example, from 0.001 to 30% by weight, preferably 0.01% by weight to 10% by weight, but in particular 0.1% by weight to 5% by weight, in each case based on the total weight of the preparations, of the active ingredients according to the invention.

The active ingredient combinations used according to the invention are particularly preferably used in pH-buffered preparations, where a pH of 5-7, in particular about 5-6, is very particularly preferred.

Also favourable are those cosmetic and dermatological preparations which are in the form of a sunscreen. In addition to one or more active ingredients according to the invention, these preferably comprise at least one UV-A filter substance and/or at least one UV-B filter substance and/or at least one inorganic pigment.

It is, however, also advantageous for the purposes of the present invention to provide cosmetic and dermatological preparations whose main purpose is not protection against sunlight, but which nevertheless comprise a content of UV protection substances. Thus, UV-A and UV-B filter substances are commonly incorporated into day creams, for example.

The cosmetic and dermatological preparations according to the invention may comprise cosmetic auxiliaries as are customarily used in such preparations, e.g. preservatives, bactericides, perfumes, antifoams, dyes, pigments which have a colouring action, thickeners, surface-active substances, emulsifiers, emollients, moisturizers and/or humectants, fats, oils, waxes and other customary constituents of a cosmetic or dermatological formulation, such as alcohols, polyols, polymers, foam stabilizers, organic solvents or silicone derivatives.

Depending on the type of product in each case, the amounts of cosmetic, dermatological or medicinal carrier substances and perfume to be used in each case can be readily determined by the person skilled in the art by simple exploratory experiments.

Preparations for the treatment and care of the skin are particularly preferred.

For use, the cosmetic and dermatological preparations according to the invention are applied to the skin and/or the hair in a sufficient amount in the manner customary for cosmetics.

Cosmetic and dermatological preparations according to the invention may exist in a variety of forms. Thus, for example, they may be a solution, an anhydrous preparation, an emulsion or microemulsion of the water-in-oil (W/O) type or of the oil-in-water (O/W) type, a multiple emulsion, for example of the water-in-oil-in-water (W/O/W) type, a gel, a solid stick, an ointment or also an aerosol. It is also advantageous to administer the active ingredients according to the invention in encapsulated form, e.g. in collagen matrices and other customary encapsulation materials, e.g. as cellulose encapsulations, in gelatin, wax matrices or liposomally encapsulated.

It is also possible and advantageous for the purposes of the present invention to incorporate the active ingredients according to the invention into aqueous systems or surfactant preparations for cleansing the skin and the hair.

In particular, the cosmetic and dermatological preparations according to the invention may also comprise antioxidants. According to the invention, favourable antioxidants which may be used are all the antioxidants which are suitable or customary for cosmetic and/or dermatological uses.

The antioxidants are advantageously chosen from the group consisting of amino acids (for example glycine, histidine, tyrosine, tryptophan) and derivatives thereof, imidazoles (for example urocanic acid) and derivatives thereof, peptides such as D,L-carnosine, D-carnosine, L-carnosine and derivatives thereof (for example anserine), carotenoids, carotenes (for example α-carotene, β-carotene, ψ-lycopene) and derivatives thereof, chlorogenic acid and derivatives thereof, lipoic acid and derivatives thereof (for example dihydrolipoic acid), aurothioglucose, propylthiouracil and other thiols (for example thioredoxin, glutathione, cysteine, cystine, cystamine and the glycosyl, N-acetyl, methyl, ethyl, propyl, amyl, butyl and lauryl, palmitoyl, oleyl, γ-linoleyl, cholesteryl and glyceryl esters thereof) and salts thereof, dilauryl thiodipropionate, distearyl thiodipropionate, thiodipropionic acid and derivatives thereof (esters, ethers, peptides, lipids, nucleotides, nucleosides and salts) and sulphoximine compounds (for example buthionine sulphoximines, homocysteine sulphoximine, buthionine sulphones, penta-, hexa- and hepta-thionine sulphoximine) in very low tolerated doses (for example pmol to µmol/kg), and furthermore (metal) chelating agents (for example α-hydroxy-fatty acids, palmitic acid, phytic acid, lactoferrin), α-hydroxy acids (for example citric acid, lactic acid, malic acid), humic acid, bile acid, bile extracts, bilirubin, biliverdin, EDTA, EGTA and derivatives thereof, unsaturated fatty acids and derivatives thereof (for example γ-linolenic acid, linoleic acid, oleic acid), folic acid and derivatives thereof, ubiquinone and ubiquinol and derivatives thereof, vitamin C and derivatives (for example ascorbyl palmitate, Mg ascorbyl phosphate, ascorbyl acetate), tocopherols and derivatives (for example vitamin E acetate), vitamin A and derivatives (vitamin A palmitate) and coniferyl benzoate of benzoin resin, rutic acid and derivatives thereof, α-glycosylrutin, ferulic acid, furfurylideneglucitol, carnosine, butylhydroxytoluene, butylhydroxyanisole, nordihydroguaiacic acid, nordihydroguaiaretic acid, trihydroxybutyrophenone, uric acid and derivatives thereof, mannose and derivatives thereof, zinc and derivatives thereof (for example ZnO, $ZnSO_4$), selenium and derivatives thereof (for example selenomethionine), stilbenes and derivatives thereof (for example stilbene oxide, trans-stilbene oxide) and the derivatives of these active ingredients mentioned which are suitable according to the invention (salts, esters, ethers, sugars, nucleotides, nucleosides, peptides and lipids).

The amount of the abovementioned antioxidants (one or more compounds) in the preparations according to the invention is preferably from 0.001 to 30% by weight, particularly preferably 0.05-20% by weight, in particular 1-10% by weight, based on the total weight of the preparation.

If vitamin E and/or derivatives thereof is or are the antioxidant or antioxidants, it is advantageous to choose the respective concentrations thereof from the range 0.001-10% by weight, based on the total weight of the formulation.

If vitamin A or vitamin A derivatives or carotenes or derivatives thereof is or are the antioxidant or antioxidants, it is advantageous to choose the respective concentrations thereof from the range 0.001-10% by weight, based on the total weight of the formulation.

Emulsions according to the invention are advantageous and comprise, for example, said fats, oils, waxes and other fatty substances, and also water and an emulsifier, as is customarily used for this type of formulation.

The lipid phase can advantageously be chosen from the following group of substances:
  mineral oils, mineral waxes;
  oils, such as triglycerides of capric or of caprylic acid, also natural oils such as, for example, castor oil;
  fats, waxes and other natural and synthetic fatty substances, preferably esters of fatty acids with alcohols of low carbon number, for example with isopropanol, propylene glycol or glycerol, or esters of fatty alcohols with alkanoic acids of low carbon number or with fatty acids;
  alkyl benzoates;
  silicone oils, such as dimethylpolysiloxanes, diethylpolysiloxanes, diphenylpolysiloxanes and mixed forms thereof.

For the purposes of the present invention, the oil phase of the emulsions, oleogels and hydrodispersions or lipodispersions is advantageously chosen from the group of esters of saturated and/or unsaturated, branched and/or unbranched alkanecarboxylic acids having a chain length of from 3 to 30 carbon atoms and saturated and/or unsaturated, branched and/or unbranched alcohols having a chain length of from 3 to 30 carbon atoms, from the group of esters of aromatic carboxylic acids and saturated and/or unsaturated, branched and/or unbranched alcohols having a chain length of from 3 to 30 carbon atoms. Such ester oils can then be advantageously chosen from the group consisting of isopropyl myristate, isopropyl palmitate, isopropyl stearate, isopropyl oleate, n-butyl stearate, n-hexyl laurate, n-decyl oleate, isooctyl stearate, isononyl stearate, isononyl isononanoate, 2-ethylhexyl palmitate, 2-ethylhexyl laurate, 2-hexyldecyl stearate, 2-octyldodecyl palmitate, oleyl oleate, oleyl erucate, erucyl oleate, erucyl erucate and synthetic, semisynthetic and natural mixtures of such esters, e.g. jojoba oil.

The oil phase can also advantageously be chosen from the group of branched and unbranched hydrocarbons and hydrocarbon waxes, silicone oils, dialkyl ethers, from the group of saturated or unsaturated, branched or unbranched alcohols, and also fatty acid triglycerides, namely the triglycerol esters of saturated and/or unsaturated, branched and/or unbranched alkanecarboxylic acids having a chain length of from 8 to 24, in particular 12-18, carbon atoms. The fatty acid triglycerides can advantageously be chosen, for example, from the group of synthetic, semi-synthetic and natural oils, e.g. olive oil, sunflower oil, soybean oil, groundnut oil, rapeseed oil, almond oil, palm oil, coconut oil, palm kernel oil and the like.

For the purposes of the present invention, any mixtures of such oil and wax components can also advantageously be used. When required, it may also be advantageous to use waxes, for example cetyl palmitate, as the sole lipid component of the oil phase.

The oil phase is advantageously chosen from the group consisting of 2-ethylhexyl isostearate, octyldodecanol, isotridecyl isononanoate, isoeicosane, 2-ethylhexyl cocoate, $C_{12-15}$-alkyl benzoate, caprylic/capric triglyceride and dicaprylyl ether.

Mixtures of $C_{12-15}$-alkyl benzoate and 2-ethylhexyl isostearate, mixtures of $C_{12-15}$-alkyl benzoate and isotridecyl isononanoate and mixtures of $C_{12-15}$-alkyl benzoate, 2-ethylhexyl isostearate and isotridecyl isononanoate are particularly advantageous.

For the purposes of the present invention, of the hydrocarbons, paraffin oil, squalane and squalene can advantageously be used.

The oil phase can advantageously also contain cyclic or linear silicone oils or can consist entirely of such oils, although it is preferable to use an additional content of other oil phase components in addition to the silicone oil or silicone oils.

Cyclomethicone (octamethylcyclotetrasiloxane) is advantageously used as the silicone oil to be used according to the invention. However, other silicone oils can also be advantageously used for the purposes of the present invention, for example hexamethylcyclotrisiloxane, polydimethylsiloxane, poly(methylphenylsiloxane).

Mixtures of cyclomethicone and isotridecyl isononanoate and mixtures of cyclomethicone and 2-ethylhexyl isostearate are particularly advantageous.

Advantageous emulsifiers are, for example, glyceryl stearate in a mixture with ceteareth-20; sorbitan stearate; sorbitan oleate; ceteareth-25; ceteareth-6 in a mixture with stearyl alcohol; cetylstearyl alcohol in a mixture with PEG-40 castor oil and sodium cetylstearyl sulphate; triceteareth-4 phosphate; glyceryl stearate; sodium cetylstearyl sulphate; lecithin; trilaureth-4 phosphate; laureth-4 phosphate; stearic acid; propylene glycol stearate SE; PEG-25 hydrogenated castor oil; PEG-54 hydrogenated castor oil; PEG-6 caprylic/capric glycerides; glyceryl oleate in a mixture with propylene glycol; PEG-9 stearate; glyceryl lanolate; ceteth-2; ceteth-20; polysorbate 60; lanolin; glyceryl stearate in a mixture with PEG-100 stearate; glyceryl myristate; microcrystalline wax (Cera microcristallina) in a mixture with paraffin oil (Paraffinum liquidum), ozokerite, hydrogenated castor oil, glyceryl isostearate and polyglyceryl-3 oleate; glyceryl laurate, PEG-40 sorbitan peroleate; laureth-4; ceteareth-3; wool wax acid mixtures; isostearyl glyceryl ether; cetylstearyl alcohol in a mixture with sodium cetylstearyl sulphate; wool wax alcohol mixtures; laureth-23; steareth-2; glyceryl stearate in a mixture with PEG-30 stearate; PEG-40 stearate; glycol distearate; PEG-22 dodecyl glycol copolymer; polyglyceryl-2 PEG-4 stearate; pentaerythrithyl isostearate; polyglyceryl-3 diisostearate; ceteareth-20; sorbitan oleate in a mixture with hydrogenated castor oil, beeswax (Cera alba) and stearic acid; sodium dihydroxycetylphosphate in a mixture with isopropyl hydroxycetyl ether; methylglucose sesquistearate; steareth-10; PEG-20 stearate; steareth-2 in a mixture with PEG-8 distearate; steareth-21; steareth-20; isosteareth-20; methylglucose dioleate; PEG-7 hydrogenated castor oil; sorbitan oleate in a mixture with PEG-2 hydrogenated castor oil, ozokerite and hydrogenated castor oil; sorbitan isostearate in a mixture with PEG-2 hydrogenated castor oil, ozokerite and hydrogenated castor oil; PEG-45/dodecyl glycol copolymer; methoxy-PEG-22/dodecyl glycol copolymer; hydrogenated coconut fatty acid glycerides; polyglyceryl-4 isostearate; PEG-40 sorbitan peroleate; PEG-40 sorbitan perisostearate; PEG-20 glyceryl stearate; PEG-20-glyceryl stearate; PEG-8 beeswax; laurylmethicone copolyol; cetyldimethicone copolyol; polyglyceryl-2 laurate; isostearyl diglyceryl succinate; stearamidopropyl PG dimonium chloride phosphate; PEG-7 hydrogenated castor oil; glyceryl stearate, ceteth-20; triethyl citrate; PEG-20 methylglucose sesquistearate; ceteareth-12; paraffin oil (Paraffinum liquidum); glyceryl stearate citrate; cetyl phosphate; sorbitan sesquioleate; acrylate/$C_{10-30}$-alkyl acrylate crosspolymer; sorbitan isostearate; methylglucose sesquistearate; triceteareth-4 phosphate; trilaureth-4 phosphate; polyglyceryl methylglucose distearate; poloxamer 101; potassium cetyl phosphate; isosteareth-10; polyglyceryl-2 sesquiisostearate; ceteth-10; polyglyceryl-2 dipolyhydroxystearate; oleth-20; isoceteth-20; glyceryl isostearate; polyglyceryl-3 diisostearate; glyceryl stearate in a mixture with ceteareth-20, ceteareth-12, cetylstearyl alcohol and cetyl palmitate; cetylstearyl alcohol in a mixture with PEG-20 stearate; glyceryl stearate; PEG-30 stearate.

If appropriate, the aqueous phase of the preparations according to the invention advantageously comprises alcohols, diols or polyols of low carbon number and ethers thereof, preferably ethanol, isopropanol, propylene glycol, glycerol, ethylene glycol, ethylene glycol monoethyl or monobutyl ether, propylene glycol monomethyl, monoethyl or monobutyl ether, diethylene glycol monomethyl or monoethyl ether and analogous products, also alcohols of low carbon number, for example ethanol, isopropanol, 1,2-propanediol and glycerol, and, in particular, one or more thickeners, which can advantageously be chosen from the group consisting of silicon dioxide, aluminium silicates, polysaccharides and derivatives thereof, for example hyaluronic acid, xanthan gum and hydroxypropylmethylcellulose, particularly advantageously from the group consisting of polyacrylates, preferably a polyacrylate from the group consisting of Carbopols, for example Carbopols of types 980, 981, 1382, 2984 and 5984, in each case individually or in combination.

In particular, mixtures of the abovementioned solvents are used. In the case of alcoholic solvents, water may be a further constituent.

Emulsions according to the invention are advantageous and comprise, for example, said fats, oils, waxes and other fatty substances, and also water and an emulsifier, as is customarily used for this type of formulation.

Gels according to the invention customarily comprise alcohols of low carbon number, for example ethanol, isopropanol, 1,2-propanediol, glycerol, and water and/or an abovementioned oil in the presence of a thickener which, in the case of oily-alcoholic gels, is preferably silicon dioxide or an aluminium silicate, and in the case of aqueous-alcoholic or alcoholic gels, is preferably a polyacrylate.

Suitable propellants for preparations according to the invention which can be sprayed from aerosol containers are the customarily known, readily volatile, liquefied propellants, for example hydrocarbons (propane, butane, isobutane), which may be used alone or in mixtures with one another. Compressed air can also be used advantageously.

Preparations according to the invention can advantageously also comprise substances which absorb UV radiation in the UVB region, the total amount of filter substances being, for example, 0.1% by weight to 30% by weight, preferably 0.5 to 10% by weight, in particular 1.0 to 6.0% by weight, based on the total weight of the preparations, in order to provide cosmetic preparations which protect the hair or skin from the entire range of ultraviolet radiation. They can also be used as sunscreen compositions for hair or skin.

If the preparations according to the invention comprise UVB filter substances, these may be oil-soluble or water-soluble. Inventively advantageous oil-soluble UVB filters are, for example:

3-benzylidenecamphor derivatives, preferably 3-(4-methylbenzylidene)camphor and 3-benzylidenecamphor;

4-aminobenzoic acid derivatives, preferably 2-ethylhexyl 4-(dimethylamino)benzoate and amyl 4-(dimethylamino)benzoate;

esters of cinnamic acid, preferably 2-ethylhexyl 4-methoxycinnamate and isopentyl 4-methoxycinnamate;

esters of salicylic acid, preferably 2-ethylhexyl salicylate, 4-isopropylbenzyl salicylate and homomenthyl salicylate, derivatives of benzophenone, preferably 2-hydroxy-4-methoxybenzophenone, 2-hydroxy-4-methoxy-4'-methylbenzophenone and 2,2'-dihydroxy-4-methoxybenzophenone;

esters of benzalmalonic acid, preferably di(2-ethylhexyl) 4-methoxybenzal-malonate and 2,4,6-trianilino(p-carbo-2'-ethyl-1'-hexyloxy)-1,3,5-triazine.

Advantageous water-soluble UVB filters are, for example:

salts of 2-phenylbenzimidazole-5-sulphonic acid, such as its sodium, potassium or its triethanolammonium salt, and the sulphonic acid itself;

sulphonic acid derivatives of benzophenones, preferably 2-hydroxy-4-methoxybenzophenone-5-sulphonic acid and its salts;

sulphonic acid derivatives of 3-benzylidenecamphor, such as, for example, 4-(2-oxo-3-bornylidenemethyl)benzenesulphonic acid, 2-methyl-5-(2-oxo-3-bornylidenemethyl)sulphonic acid and their salts, and also 1,4-di(2-oxo-10-sulpho-3-bornylidenemethyl)benzene and its salts (the corresponding 10-sulphato compounds, for example the corresponding sodium, potassium or triethanolammonium salt) also referred to as benzene-1,4-di(2-oxo-3-bornylidenemethyl)-10-sulphonic acid.

The list of said UVB filters which can be used in combination with the active ingredient combinations according to the invention is not of course intended to be limiting.

The invention also provides for the use of a combination of the active ingredient combinations used according to the invention with at least one UVB filter as an antioxidant and for the use of a combination of the active ingredient combinations used according to the invention with at least one UVB filter as an antioxidant in a cosmetic or dermatological preparation.

It may also be advantageous to combine the active ingredient combinations used according to the invention with UVA filters which have to date customarily been present in cosmetic preparations. These substances are preferably derivatives of dibenzoylmethane, in particular 1-(4'-tert-butylphenyl)-3-(4'-methoxyphenyl)propane-1,3-dione and 1-phenyl-3-(4'-isopropylphenyl)propane-1,3-dione. These combinations and preparations comprising these combinations are also provided by the invention. The amounts which may be used are as for the UVB combination.

The invention also provides for the use of a combination of active ingredient combinations used in accordance with the invention with at least one UVA filter as antioxidant, and the use of a combination of the active ingredient combinations according to the invention with at least one UVA filter as antioxidant in a cosmetic or dermatological preparation.

The invention also provides for the use of a combination of active ingredient combinations used in accordance with the invention With at least one UVA filter and at least one UVB filter as antioxidant, and the use of a combination of active ingredient combinations with at least one UVA filter and at least one UVB filter as antioxidant in a cosmetic or dermatological preparation.

Cosmetic and dermatological preparations having an effective content of active ingredient combinations used according to the invention can also comprise inorganic pigments which are normally used in cosmetics for protecting the skin against UV rays. These are oxides of titanium, zinc, zirconium, silicon, manganese, cerium and mixtures thereof, and modifications in which the oxides are the active agents. Particular preference is given to pigments based on titanium dioxide.

These combinations of UVA filters and pigment or preparations which comprise this combination are also provided by the invention. Amounts which may be used are the amounts given for the above combinations.

The cosmetic and dermatological preparations for protecting the hair against UV rays according to the invention are, for example, shampoos, preparations which are applied while rinsing the hair before or after shampooing, before or after permanent wave treatment, before or after colouring or bleaching the hair, preparations for blow-drying or arranging the hair, preparations for colouring or bleaching, a styling and treatment lotion, a hair lacquer or permanent waving agent.

The cosmetic and dermatological preparations comprise active ingredients and auxiliaries, as are customarily used for this type of preparation for hair care and hair treatment. Auxiliaries which can be used are preservatives, surface-active substances, antifoams, thickeners, emulsifiers, fats, oils, waxes, organic solvents, bactericides, perfumes, dyes or pigments whose task is to color the hair or the cosmetic or dermatological preparation itself.

The anions according to the invention are preferably chosen from the group of chlorides, sulphates and hydrogensulphates, phosphates, hydrogenphosphates and linear and cyclic oligophosphates, and carbonates and hydrogencarbonates.

Cosmetic preparations which are in the form of a skin-cleansing composition or shampoo preferably comprise at least one anionic, nonionic or amphoteric surface-active substance, or else mixtures of such substances, the active ingredient combinations used according to the invention in an aqueous medium and auxiliaries as are customarily used for this purpose. The surface-active substance or the mixtures of these substances may be present in the shampoo in a concentration between 1% by weight and 50% by weight.

If the cosmetic or dermatological preparations are in the form of a lotion which is rinsed out and applied, for example, before or after bleaching, before or after shampooing, between two shampooing steps, before or after a permanent wave treatment, then they are, for example, aqueous or aqueous-alcoholic solutions which optionally comprise surface-active substances, the concentration of which can be between 0.1 and 10% by weight, preferably between 0.2 and 5% by weight.

These cosmetic or dermatological preparations can also be aerosols with auxiliaries customarily used for this purpose.

A cosmetic preparation in the form of a lotion which is not rinsed out, in particular a lotion for arranging the hair, a lotion which is used during blow-drying of the hair, a styling and treatment lotion, is generally an aqueous, alcoholic or aqueous-alcoholic solution and comprises at least one cationic, anionic, nonionic or amphoteric polymer or else mixtures thereof, and also active ingredient combinations used according to the invention in effective concentration. The amount of polymers used is, for example, between 0.1 and 10% by weight, preferably between 0.1 and 3% by weight.

Cosmetic preparations for the treatment and care of the hair which contain the active ingredient combinations used according to the invention can be in the form of emulsions which are of the nonionic or anionic type. Nonionic emulsions contain, in addition to water, oils or fatty alcohols which may, for example, also be polyethoxylated or polypropoxylated, or else mixtures of the two organic components. These emulsions optionally comprise cationic surface-active substances.

According to the invention, cosmetic preparations for the treatment and care of hair may be in the form of gels which, as well as comprising an effective content of active ingredients according to the invention and optionally solvents customarily used for this purpose, preferably water, also comprise organic thickeners, e.g. gum arabic, xanthan gum, sodium alginate, cellulose derivatives, preferably methylcellulose, hydroxymethylcellulose, hydroxyethylcellulose, hydroxypropylcellulose, hydroxypropylmethylcellulose or inorganic thickeners, e.g. aluminium silicates, such as, for example, bentonites, or a mixture of polyethylene glycol and polyethylene glycol stearate or distearate. The thickener is present in the gel, for example, in an amount between 0.1 and 30% by weight, preferably between 0.5 and 15% by weight:

Preferably, the amount of active ingredients according to the invention in a composition intended for hair is 0.05% by weight to 10% by weight, in particular 0.5% by weight to 5% by weight, based on the total weight of the composition.

Aqueous cosmetic cleansing compositions according to the invention or low-water or anhydrous cleansing composition concentrates intended for aqueous cleansing can comprise anionic, nonionic and/or amphoteric surfactants.

Surfactants are amphiphilic substances which can dissolve organic nonpolar substances in water. As a result of their specific molecular structure having at least one hydrophilic molecular moiety and one hydrophobic molecular moiety, they are able to reduce the surface tension of the water, wet the skin, facilitate the removal and dissolution of soiling, facilitate rinsing and, if desired, control foaming.

The hydrophilic moieties of a surfactant molecule are mostly polar functional groups, for example $—COO^-$, $—OSO_3^{2-}$, $—SO_3^-$, while the hydrophobic moieties are usually nonpolar hydrocarbon radicals. Surfactants are generally classified according to the type and charge of the hydrophilic molecular moiety. In this connection, it is possible to differentiate between four groups:

anionic surfactants,
cationic surfactants,
amphoteric surfactants and
nonionic surfactants.

Anionic surfactants usually have, as functional groups, carboxylate, sulphate or sulphonate groups. In aqueous solution, they form negatively charged organic ions in an acidic or neutral medium. Cationic surfactants are characterized almost exclusively by the presence of a quaternary ammonium group. In aqueous solution, they form positively charged organic ions in an acidic or neutral medium. Amphoteric surfactants contain both anionic and cationic groups and accordingly in aqueous solution exhibit the behaviour of anionic or cationic surfactants depending on the pH. In a strongly acidic medium, they have a positive charge, and in an alkaline medium a negative charge. By contrast, in the neutral pH range, they are zwitterionic, as the example below serves to illustrate:

$RNH_2^+CH_2CH_2COOHX^-$ (at pH=2) $X^-$=any anion, e.g. $Cl^-$
$RNH_2^+CH_2CH_2COO^-$ (at pH=7)
$RNHCH_2CH_2COO^-$ $B^+$ (at pH=12) $B^+$=any cation, e.g. $Na^+$ Polyether chains are typical of nonionic surfactants. Nonionic surfactants do not form ions in an aqueous medium.

A. Anionic Surfactants

Anionic surfactants which can be used advantageously are acylamino acids (and salts thereof), such as
1. acyl glutamates, for example sodium acyl glutamate, di-TEA-palmitoyl aspartate and sodium caprylic/capric glutamate,
2. acylpeptides, for example palmitoyl-hydrolyzed milk protein, sodium cocoyl-hydrolyzed soya protein and sodium/potassium cocoyl-hydrolyzed collagen,
3. sarcosinates, for example myristoyl sarcosinate, TEA-lauroyl sarcosinate, sodium lauroyl sarcosinate and sodium cocoyl sarcosinate,
4. taurates, for example sodium lauroyl taurate and sodium methylcocoyl taurate,
5. acyl lactylates, lauroyl lactylate, caproyl lactylate
6. alaninates Carboxylic Acids and Derivatives, such as
1. carboxylic acids, for example lauric acid, aluminium stearate, magnesium alkanolate and zinc undecylenate,
2. ester carboxylic acids, for example calcium stearoyl lactylate, laureth-6 citrate and sodium PEG-4 lauramide carboxylate,
3. ether carboxylic acids, for example sodium laureth-13 carboxylate and sodium PEG-6 cocamide carboxylate, Phosphoric Esters and Salts, such as, for Example, DEA-Oleth-10 Phosphate and Dilaureth-4 Phosphate, Sulphonic Acids and Salts, such as
1. acyl isethionates, e.g. sodium/ammoniumcocoyl isethionate,
2. alkylarylsulphonates,
3. alkylsulphonates, for example sodium cocomonoglyceride sulphate, sodium $C_{12-14}$-olefin sulphonate, sodium lauryl sulphoacetate and magnesium PEG-3 cocamide sulphate,
4. sulphosuccinates, for example dioctyl sodium sulphosuccinate, disodium laureth sulphosuccinate, disodium lauryl sulphosuccinate and disodium undecyleneamido-MEA sulphosuccinate and Sulphuric Esters, such as
1. alkyl ether sulphates, for example sodium, ammonium, magnesium, MIPA, TIPA laureth sulphate, sodium myreth sulphate and sodium $C_{12-13}$ pareth sulphate,
2. alkyl sulphates, for example sodium, ammonium and TEA lauryl sulphate.

B. Cationic Surfactants

Cationic surfactants which can be used advantageously are
1. alkylamines,
2. alkylimidazoles,
3. ethoxylated amines and
4. quaternary surfactants,
5. ester quats Quaternary surfactants contain at least one N atom which is covalently bonded to 4 alkyl and/or aryl groups. Irrespective of the pH, this leads to a positive charge. Alkylbetaine, alkylamidopropylbetaine and alkylamidopropylhydroxysultaine are advantageous quaternary surfactants. The cationic surfactants used according to the invention can also preferably be chosen from the group of quaternary ammonium compounds, in particular benzyltrialkylammonium chlorides or bromides, such as, for example, benzyldimethylstearylammonium chloride, and also alkyltrialkylammonium salts, for example cetyltrimethylammonium chloride or bromide, alkyldimethylhydroxyethylammonium chlorides or bromides, dialkyldimethylammonium chlorides or bromides, alkylamidoethyltrimethylammonium ether sulphates, alkylpyridinium salts, for example lauryl- or cetylpyridinium chloride, imidazoline derivatives and compounds having cationic character, such as amine oxides, for example alkyldimethylamine oxides or alkylaminoethyidimethylamine oxides. In particular the use of cetyltrimethylammonium salts is advantageous.

C. Amphoteric Surfactants

Amphoteric surfactants which can be used advantageously are
1. acyl/dialkylethylenediamine, for example sodium acyl amphoacetate, disodium acyl amphodipropionate, disodium alkyl amphodiacetate, sodium acyl amphohydroxypropylsulphonate, disodium acyl amphodiacetate and sodium acyl amphopropionate,
2. N-alkylamino acids, for example aminopropylalkylglutamide, alkylaminopropionic acid, sodium alkylimidodipropionate and lauroamphocarboxyglycinate.

D. Nonionic Surfactants

Nonionic surfactants which can be used advantageously are
1. alcohols,
2. alkanolamides, such as cocamides MEA/DEA/MIPA,
3. amine oxides, such as cocoamidopropylamine oxide, 4. esters which are formed by esterification of carboxylic acids with ethylene oxide, glycerol, sorbitol or other alcohols,
5. ethers, for example ethoxylated/propoxylated alcohols, ethoxylated/propoxylated esters, ethoxylated/propoxylated glycerol esters, ethoxylated/propoxylated cholesterols, ethoxylated/propoxylated triglyceride esters, ethoxylated/propoxylated lanolin, ethoxylated/propoxylated polysiloxanes, propoxylated POE ethers and alkyl polyglycosides, such as lauryl glucoside, decyl glycoside and cocoglycoside.
6. sucrose esters, sucrose ethers
7 polyglycerol esters, diglycerol esters, monoglycerol esters
8. methylglucose esters, esters of hydroxy acids Also advantageous is the use of a combination of anionic and/or amphoteric surfactants with one or more nonionic surfactants.

Cosmetic preparations which are in the form of cosmetic cleansing preparations for the skin may be in liquid or solid form. As well as comprising active ingredient combinations used in accordance with the invention, they preferably comprise at least one anionic, nonionic or amphoteric surface-active substance or mixtures thereof, and auxiliaries as are customarily used for this purpose. The surface-active substance can be present in the cleansing preparations in a concentration between 1 and 94% by weight, based on the total weight of the preparations.

Cosmetic preparations which are in the form of a shampoo comprise, in addition to an effective content of active ingredient combinations, preferably at least one anionic, nonionic or amphoteric surface-active substance or mixtures thereof, and auxiliaries as are customarily used therefor. The surface-active substance can be present in the shampoo in a concentration between 1% by weight and 94% by weight.

Apart from the abovementioned surfactants, the compositions according to the invention comprise water and optionally the additives customary in cosmetics, for example perfume, thickeners, dyes, deodorants, antimicrobial substances, refatting agents, complexing agents and sequestering agents, pearlescent agents, plant extracts, vitamins, active ingredients and the like.

It is preferred according to the invention to add those active ingredient combinations comprising complexing agents to the active ingredient combinations used according to the invention or cosmetic or dermatological preparations.

Complexing agents are auxiliaries of cosmetology and/or medicinal galenics which are known per se. The complexing of troublesome metals such as Mn, Fe, Cu and others can prevent, for example, undesired chemical reactions in cosmetic or dermatological preparations.

Complexing agents, in particular chelating agents, form complexes with metal atoms. In the presence of one or more polybasic complexing agents, i.e. chelating agents, these complexes are metallacycles. Chelates are compounds in which a single ligand occupies more than one coordination site on a central atom. In this case, normally extended compounds are thus closed as a result of complex formation via a metal atom or ion to give rings. The number of bonded ligands depends on the coordination number of the central metal. A prerequisite for the formation of a chelate is that the compound reacting with the metal contains two or more atomic groupings which act as electron donors.

The complexing agent(s) can advantageously be chosen from the group of customary compounds, at least one substance preferably being chosen from the group consisting of tartaric acid and anions thereof, citric acid and anions thereof, aminopolycarboxylic acids and anions thereof (such as, for example, ethylenediaminetetraacetic acid (EDTA) and anions thereof, nitrilotriacetic acid (NTA) and anions thereof, hydroxyethylenediaminotriacetic acid (HOEDTA) and anions thereof, diethyleneaminopentaacetic acid (DPTA) and anions thereof, trans-1,2-diaminocyclohexanetetraacetic acid (CDTA) and anions thereof).

The complexing agent or the complexing agents are, according to the invention, advantageously present in cosmetic or dermatological preparations preferably in an amount of from 0.01% by weight to 10% by weight, preferably in an amount of from 0.05% by weight to 5% by weight, particularly preferably in an amount of 0.1-2.0% by weight, based on the total weight of the preparations.

The present invention likewise also covers a method of protecting cosmetic or dermatological preparations against oxidation or photooxidation where these preparations are, for example, preparations for the treatment and care of the hair, in particular hair colourants, hair lacquers, shampoos, colour shampoos, and also make-up products, such as, for example, nail varnishes, lipsticks, foundations, washing and shower preparations, creams for the treatment or care of the skin or all other cosmetic preparations whose constituents may be associated with stability problems because of oxidation or photooxidation during storage, characterized in that the cosmetic preparations have an effective content of active ingredient combinations used according to the invention.

The amount of active ingredient combinations used according to the invention in these preparations is preferably 0.01-30% by weight, more preferably 0.05-20% by weight, in particular 0.1-10.0% by weight, based on the total weight of the preparations.

The invention also provides the process for the preparation of the cosmetic compositions according to the invention, which is characterized in that active ingredient combinations according to the invention are incorporated into cosmetic and dermatological formulations in a manner known per se.

Unless stated otherwise, all amounts, proportions and percentages are based on the weight and the total amount or on the total weight of the preparations.

DETAILED DESCRIPTION OF THE INVENTION

The examples below serve to illustrate the present invention without limiting it.

Example 1

| O/W cream | |
|---|---|
| | % by wt. |
| Glyceryl stearate | 3.0000 |
| Cetyl alcohol | 3.0000 |
| PEG-40 stearate | 3.5000 |
| Paraffinum liquidum | 5.0000 |
| C12-15 Alkyl benzoate | 0.5000 |
| Cyclomethicone | 5.0000 |
| Glycerol | 5.0000 |

-continued

O/W cream

|  | % by wt. |
| --- | --- |
| Sodium chloride | 5.0000 |
| Sodium Chloride | 5.0000 |
| L-carnitine | 0.5000 |
| Dyes/perfume | q.s. |
| Preservative | |
| Water | ad 100.0000 |

The constituents of the oil phase are combined together, then stirred at 60-70° C. with the likewise combined water phase, and then the mixture is homogenized. It is then cooled to room temperature.

Example 2

O/W cream

|  | % by wt. |
| --- | --- |
| Glyceryl stearate | 2.4000 |
| Cetyl alcohol | 2.4000 |
| Glyceryl stearate + PEG-100 stearate | 1.2000 |
| Paraffinum liquidum | 15.0000 |
| Xanthan gum | 0.2000 |
| Glycerol | 3.0000 |
| Glycerin | 5.0000. |
| TaurinAcetyl-L-carnitine | 0.30000 |
| Sodium chloride | 55.0000 |
| Sodium Chloride | |
| Diazolidinylurea | 0.3000 |
| Dyes/perfume | q.s. |
| Preservative | |
| Water | ad 100.0000 |

The constituents of the oil phase are combined together, then stirred at 60-70° C. with the likewise combined water phase, and then the mixture is homogenized. It is then cooled to room temperature.

Example 3

O/W cream

|  | % by wt. |
| --- | --- |
| Cetyl alcohol | 2.4000 |
| Steareth-21 | 1.2000 |
| Steareth-2 | 2.4000 |
| Paraffinum liquidum | 15.0000 |
| Xanthan gum | 0.2000 |
| Glycerol | 5.0000 |
| Urea | 2.00005. |
| Propionyl-L-carnitine | 5.00000 |
| Sodium Chloride | |
| Sodium chloride | 5.0000 |
| Diazolidinylurea | 0.3000 |
| Dyes/perfume | q.s. |
| Preservative | |
| Water | ad 100.0000 |

The constituents of the oil phase are combined together, then stirred at 60-70° C. with the likewise combined water phase, and then the mixture is homogenized. It is then cooled to room temperature.

Example 4

O/W cream

|  | % by wt. |
| --- | --- |
| Cetyl alcohol | 2.4000 |
| Steareth-21 | 1.2000 |
| Steareth-2 | 2.4000 |
| Octyldodecanol | 0.1000 |
| PPG-14 butyl ether | 5.0000 |
| Cyclomethicone | 5.0000 |
| Trisodium EDTA | 1.5000 |
| ol | 3 |
| L-carnitine fumarate | 2.0 |
| Sodium chloride | 3.0000 |
| Dyes/perfume | q.s. |
| Preservative | |
| Water | ad 100.0000 |

The constituents of the oil phase are combined together, then stirred at 60-70° C. with the likewise combined water phase, and then the mixture is homogenized. It is then cooled to room temperature.

What is claimed is:

1. A cosmetic or dermatological composition, wherein the composition comprises from 0.001% to 30% by weight of at least one substance which is a carboxylic acid ester of L-carnitine selected from propionyl-L-carnitine, L-carnitine fumarate, and L-carnitine galactarate or is an ester of carnitine with an alkanol and wherein the composition is present as at least one of an anhydrous preparation, an emulsion, a microemulsion, a multiple emulsion, a cream, a milk, a lotion, an ointment, a gel, a solid stick, and an aerosol.

2. The composition of claim 1, wherein the at least one substance is present in a concentration of from 0.05% to 10% by weight.

3. The composition of claim 1, wherein the at least one substance is present in a concentration of from 0.1% to 5.0% by weight.

4. The composition of claim 1, wherein the composition comprises from 0.05% to 10% by weight of at least one of propionyl-L-carnitine, L-carnitine fumarate, and L-carnitine galactarate.

5. The composition of claim 1, wherein the composition is a pH-buffered composition.

6. The composition of claim 1, wherein the composition has a pH of from 5 to 7.

7. The composition of claim 6, wherein the composition has a pH of from 5 to 6.

8. The composition of claim 1, wherein the composition comprises propionyl-L-carnitine.

9. The composition of claim 1, wherein the composition comprises L-carnitine fumarate.

10. The composition of claim 1, wherein the composition comprises L-carnitine galactarate.

11. The composition of claim 1, wherein the composition comprises an ester of carnitine with an alkanol.

12. A cosmetic or dermatological composition, wherein the composition has a pH of from 5 to 7 and comprises from 0.05% to 10% by weight of at least one substance which comprises a carboxylic acid ester of L-carnitine selected from propionyl-L-carnitine, L-carnitine fumarate, and L-carnitine galactarate or is an ester of carnitine with an alkanol.

13. The composition of claim 12, wherein the at least one substance is present in a concentration of from 0.1% to 5.0% by weight.

14. The composition of claim 12, wherein the composition is present as an emulsion.

15. The composition of claim 14, wherein the composition is present as an oil-in-water emulsion.

16. The composition of claim 12, wherein the composition has a pH of from 5 to 6.

17. The composition of claim 12, wherein the composition comprises propionyl-L-carnitine.

18. The composition of claim 12, wherein the composition comprises L-carnitine fumarate.

19. The composition of claim 12, wherein the composition comprises L-carnitine galactarate.

20. A cosmetic or dermatological composition, wherein the composition comprises from 0.1% to 5.0% by weight of at least one substance which is an ester of carnitine with a carboxylic acid, or an ester of carnitine with an alkanol, has a pH of from 5 to 6, and is present as at least one of an anhydrous preparation, an emulsion, a microemulsion, a multiple emulsion, a cream, a milk, a lotion, an ointment, a gel, a solid stick, and an aerosol, the at least one substance comprising at least one of propionyl-L-carnitine, L-carnitine fumarate, and L-carnitine galactarate.

21. The composition of claim 20, wherein the composition is present as an emulsion.

22. The composition of claim 21, wherein the composition is present as an oil-in-water emulsion.

23. The composition of claim 20, wherein the composition comprises propionyl-L-carnitine.

24. The composition of claim 20, wherein the composition comprises L-carnitine fumarate.

25. The composition of claim 20, wherein the composition comprises L-carnitine galactarate.

* * * * *